(12) United States Patent
Villain et al.

(10) Patent No.: US 7,662,914 B2
(45) Date of Patent: Feb. 16, 2010

(54) NATIVE CHEMICAL LIGATION WITH THREE OR MORE COMPONENTS

(75) Inventors: Matteo Villain, Nyon (CH); Hubert Gaertner, Archamps (CH)

(73) Assignee: Amylin Pharmaceuticals, Inc., San Diego, CA (US)

( * ) Notice: Subject to any disclaimer, the term of this patent is extended or adjusted under 35 U.S.C. 154(b) by 579 days.

(21) Appl. No.: 10/476,447

(22) PCT Filed: May 31, 2002

(86) PCT No.: PCT/IB02/02949

§ 371 (c)(1),
(2), (4) Date: Aug. 16, 2004

(87) PCT Pub. No.: WO02/098902

PCT Pub. Date: Dec. 12, 2002

(65) Prior Publication Data

US 2005/0064538 A1    Mar. 24, 2005

(30) Foreign Application Priority Data

Jun. 5, 2001    (GB) ................................. 0113657.1

(51) Int. Cl.
*A61K 38/00*    (2006.01)
(52) U.S. Cl. .................................................... 530/333
(58) Field of Classification Search ........................ None
See application file for complete search history.

(56) References Cited

U.S. PATENT DOCUMENTS 6,372,912 B1    4/2002    Doring et al.

FOREIGN PATENT DOCUMENTS

| DE | 19919336 | 11/2000 |
|---|---|---|
| JP | 2000-309572 A | 11/2000 |

OTHER PUBLICATIONS

Villain et al Chemical Ligation of Multiple Peptide Fragments Using a New Protection Strategy, Peptides: Wave of the Future (2001), p. 107.*
Tam JP. "Tandem ligation of unprotected peptides through thiaprolyl and cysteinyl bonds in water," J Am Chem Soc. Mar. 21, 2001;123(11):2487-94.*
Mitchell, et al., Int J Peptide Protein Res, 36(4): 350-355 (1990).

* cited by examiner

*Primary Examiner*—Cecilia Tsang
*Assistant Examiner*—Thomas S Heard

(57) ABSTRACT

The invention provides a method of assembling oligopeptide intermediates in a native chemical ligation reaction that eliminates self-ligation of bi-functional intermediates. An important aspect of the invention is a bi-functional intermediate with an N-terminal cyclic thiazolidine protecting group which effectively prevents self-ligation in the chemical assembly process. The present invention is useful in methods for convergent synthesis of polypeptides and proteins and improves the efficiency of native chemical ligation reactions, particularly where three or more peptide fragments are used to assemble a polypeptide or protein product.

8 Claims, 13 Drawing Sheets

FIG. 2

Leu Arg Pro Gly Asp Cys Glu Val Cys Ile Ser Tyr Leu Gly Arg Phe
                5                  10                 15

Tyr Gln Asp Leu Lys Asp Arg Asp Val Thr Phe Ser Pro Ala Thr Ile
            20              25              30

Glu Asn Glu Leu Ile Lys Phe Cys Arg Glu Ala Arg Gly Lys Glu Asn
        35              40              45

Arg Leu Cys Tyr Tyr Ile Gly Ala Thr Asp Asp Ala Ala Thr Lys Ile
    50              55              60

Ile Asn Glu Val Ser Lys Pro Leu Ala His His Ile Pro Val Glu Lys
65              70              75              80

Ile Cys Glu Lys Leu Lys Lys Lys Asp Ser Gln Ile Cys Glu Leu Lys
            85              90              95

Tyr Asp Lys Gln Ile Asp Leu Ser Thr Val Asp Leu Lys Lys Leu Arg
            100             105             110

Val Lys Glu Leu Lys Lys Ile Leu Asp Asp Trp Gly Glu Thr Cys Lys
        115             120             125

Gly Cys Ala Glu Lys Ser Asp Tyr Ile Arg Lys Ile Asn Glu Leu Met
        130             135             140

Pro Lys Tyr Ala Pro Lys Ala Ala Ser Ala Arg Thr Asp Leu
145             150             155

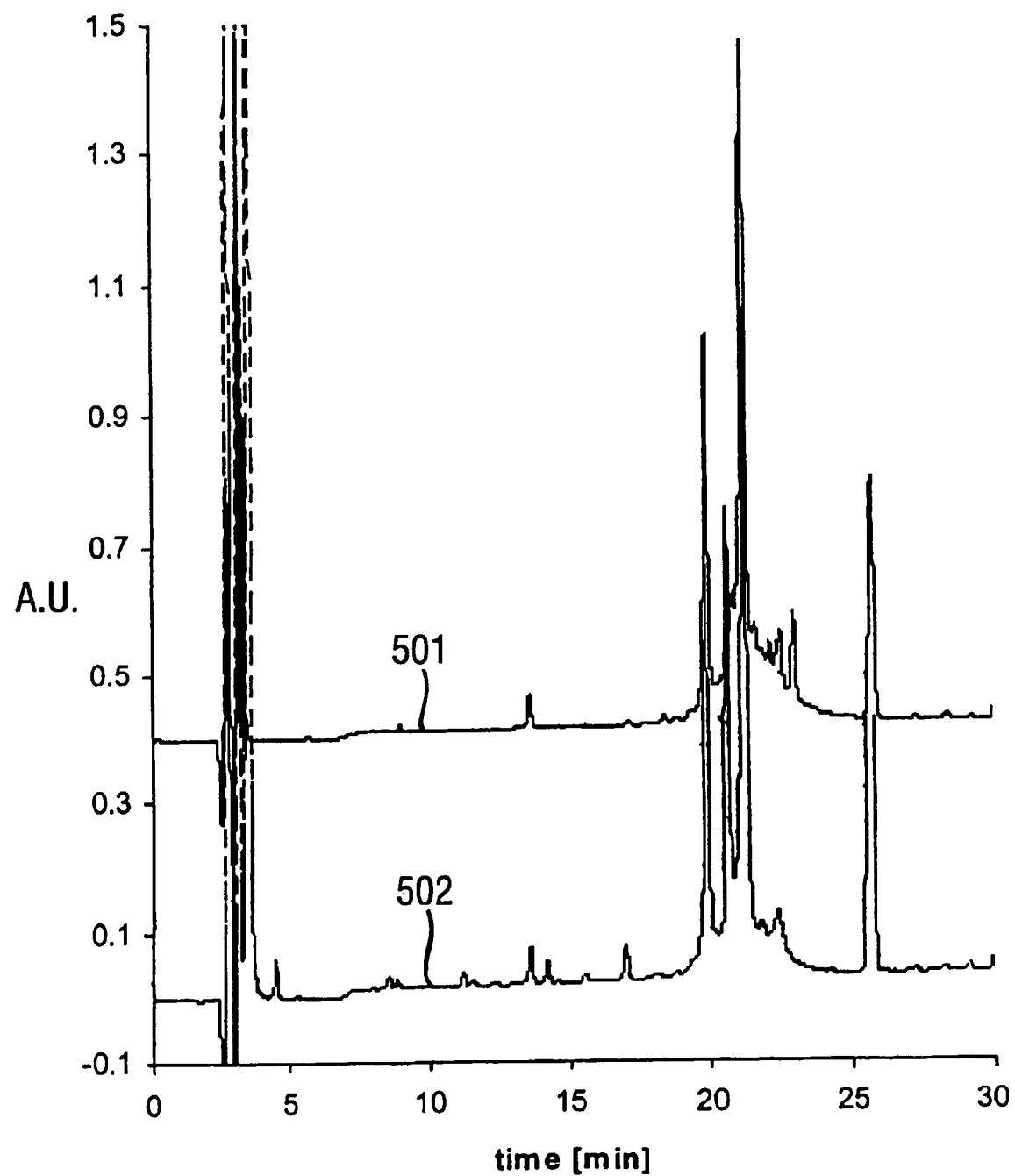

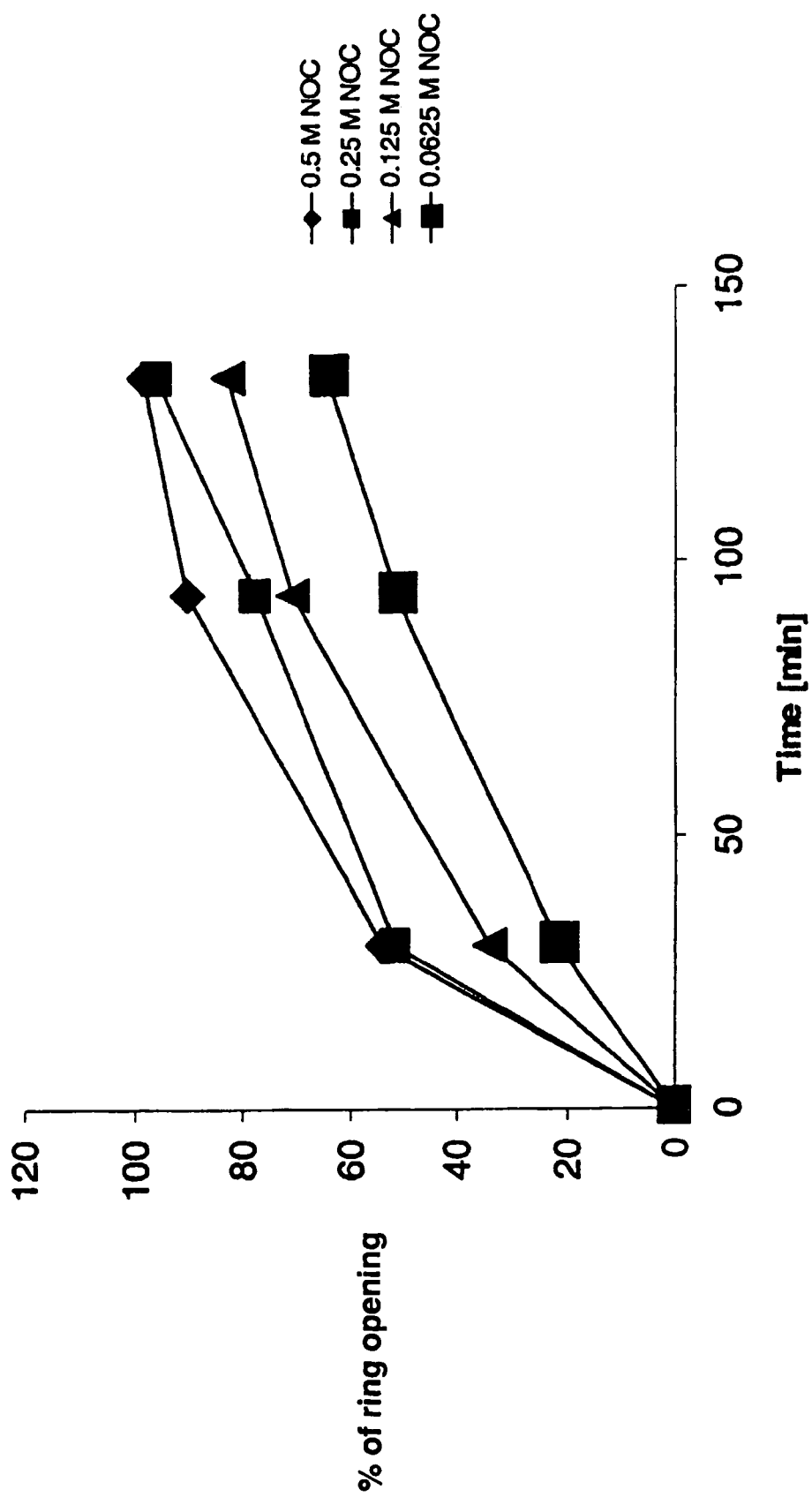

SEQUENCE LISTING

```
<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence:synthesized
      oligopeptide intermediate fragment 1

<400> SEQUENCE: 1

Cys Ala Glu Lys Ser Asp Tyr Ile Arg Lys Ile Asn Glu Leu Met Pro
  1               5                  10                  15

Lys Tyr Ala Pro Lys Ala Ala Ser Ala Arg Thr Asp Leu
             20                  25

<210> SEQ ID NO 2
<211> LENGTH: 48
<212> TYPE: PRT
<213> ORGANISM: Artificial Sequence
<220> FEATURE:
<223> OTHER INFORMATION: Description of Artificial Sequence:synthesized
      oligopeptide intermediate fragment 2
<220> FEATURE:
<221> NAME/KEY: MOD_RES
<222> LOCATION: (1)
<223> OTHER INFORMATION: Xaa = thioproline
<220> FEATURE:
<221> NAME/KEY: MOD_RES
<222> LOCATION: (48)
<223> OTHER INFORMATION: Xaa = glycine thiophenylester

<400> SEQUENCE: 2

Xaa Glu Lys Leu Lys Lys Lys Asp Ser Gln Ile Cys Glu Leu Lys Tyr
  1               5                  10                  15

Asp Lys Gln Ile Asp Leu Ser Thr Val Asp Leu Lys Lys Leu Arg Val
             20                  25                  30

Lys Glu Leu Lys Lys Ile Leu Asp Asp Trp Gly Glu Thr Cys Lys Xaa
         35                  40                  45
```

```
<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence:synthesized
      oligopeptide intermediate fragment 3
<220> FEATURE:
<221> NAME/KEY: MOD_RES
<222> LOCATION: (1)
<223> OTHER INFORMATION: Xaa = thioproline
<220> FEATURE:
<221> NAME/KEY: MOD_RES
<222> LOCATION: (42)
<223> OTHER INFORMATION: Xaa = isoleucine thiophenylester

<400> SEQUENCE: 3

Xaa Arg Glu Ala Arg Gly Lys Glu Asn Arg Leu Cys Tyr Tyr Ile Gly
 1               5                  10                  15

Ala Thr Asp Asp Ala Ala Thr Lys Ile Ile Asn Glu Val Ser Lys Pro
            20                  25                  30

Leu Ala His His Ile Pro Val Glu Lys Xaa
        35                  40

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence:synthesized
      oligopeptide intermediate fragment 4
<220> FEATURE:
<221> NAME/KEY: MOD_RES
<222> LOCATION: (39)
<223> OTHER INFORMATION: Xaa = phenylalanine thiophenylester

<400> SEQUENCE: 4

Leu Arg Pro Gly Asp Cys Glu Val Cys Ile Ser Tyr Leu Gly Arg Phe
 1               5                  10                  15

Tyr Gln Asp Leu Lys Asp Arg Asp Val Thr Phe Ser Pro Ala Thr Ile
            20                  25                  30

Glu Asn Glu Leu Ile Lys Xaa
        35

<210> SEQ ID NO 5
<211> LENGTH: 157
<212> TYPE: PRT
<213> ORGANISM: Artificial Sequence
<220> FEATURE:
<223> OTHER INFORMATION: Description of Artificial Sequence:synthetic
      polypeptide assembled from four oligopeptide
      intermediates

<400> SEQUENCE: 5

Leu Arg Pro Gly Asp Cys Glu Val Cys Ile Ser Tyr Leu Gly Arg Phe
 1               5                  10                  15

Tyr Gln Asp Leu Lys Asp Arg Asp Val Thr Phe Ser Pro Ala Thr Ile
            20                  25                  30

Glu Asn Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65                  70                  75                  80
```

```
Ile Cys Glu Lys Leu Lys Lys Lys Asp Ser Gln Ile Cys Glu Leu Lys
            85                  90                  95

Tyr Asp Lys Gln Ile Asp Leu Ser Thr Val Asp Leu Lys Lys Leu Arg
                100             105                 110

Val Lys Glu Leu Lys Lys Ile Asp Asp Trp Gly Glu Thr Cys Lys Gly
            115             120                 125

Cys Ala Glu Lys Ser Asp Tyr Ile Arg Lys Ile Asn Glu Leu Met Pro
            130             135             140

Lys Tyr Ala Pro Lys Ala Ala Ser Ala Arg Thr Asp Leu
145                 150             155

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:synthesized
      polypeptide

<400> SEQUENCE: 6

Cys Tyr Ala Lys Tyr Ala Lys Leu
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:synthesized
      polypeptide
<220> FEATURE:
<221> NAME/KEY: MOD_RES
<222> LOCATION: (1)
<223> OTHER INFORMATION: Xaa = thioproline

<400> SEQUENCE: 7

Xaa Tyr Ala Lys Tyr Ala Lys Leu
  1               5
```

NATIVE CHEMICAL LIGATION WITH THREE OR MORE COMPONENTS

FIELD OF THE INVENTION

The invention relates generally to methods for synthesizing polypeptides and proteins, and more particularly, to a method and intermediates for covalently assembling multiple peptide fragments into a full length polypeptide.

BACKGROUND

The sequencing of the human genome has created the promise and opportunity for understanding the function of all genes and proteins relevant to human biology and disease, Peltonen and McKusick, Science, 291: 1224-1229 (2001). However, several important hurdles must be overcome before this promise can be fully attained. First, the sequence signals that indicate the location of a gene in the genome and that control its expression are not well understood, so it is frequently difficult to predict the presence of a gene that is actually transcribed, e.g. Guigo et al, Genome Res., 10: 1631-1642 (2000); Rudd et al, Electrophoresis, 19:536-544 (1998). Second, although monitoring gene expression at the transcript level has become more robust with the development of microarray technology, numerous problems still exist including variability relating to probe hybridization differences and cross-reactivity, element-to-element differences within microarrays, and microarray-to-microarray differences, e.g. Audic and Claverie, Genome Res., 7: 986-995 (1997); Wittes and Friedman, J. Natl. Cancer Inst., 91: 400-401 (1999); Richmond et al, Nucleic Acids Research, 27: 3821-3835 (1999). Finally, because of the scale of human molecular biology (about a third of the estimated 30-40 thousand genes appear to give rise to multiple splice variants and most appear to encode protein products with a plethora of post-translational modifications), potentially many tens of thousands of genes and their expression products will have to be isolated and tested in order to understand their role in health and disease, Dawson and Kent, Annu. Rev. Biochem., 69: 923-960 (2000).

In regard to the issue of scale, the application of conventional recombinant methodologies for cloning, expressing, recovering, and isolating proteins are still time consuming and labor-intensive processes, so that their application in screening large numbers of different gene products for determining function has been limited. Recently, a convergent synthesis approach has been developed which may address the need for facile access to highly purified research-scale amounts of protein for functional screening, Dawson and Kent (cited above); Dawson et al, Science, 266: 776-779 (1994). In its most attractive implementation, an unprotected oligopeptide intermediate having a C-terminal thioester reacts with an N-terminal cysteine of another oligopeptide intermediate under mild aqueous conditions to form a thioester linkage which spontaneously rearranges to a natural peptide linkage, Kent et al, U.S. Pat. No. 6,184,344. The approach has been used to assemble oligopeptides into active proteins both in solution phase, e.g. Kent et al, U.S. Pat. No. 6,184,344, and on a solid phase support, e.g. Canne et al, J. Am. Chem. Soc., 121: 8720-8727 (1999).

When the polypeptide to be synthesized by this approach exceeds 100-150 amino acids, it is necessary to join three or more fragments, as it is currently difficult to synthesize and purify oligopeptide intermediates longer than about 60 residues. In this case, the internal oligopeptide intermediates not only contain a C-terminal thioester moiety, but also an N-terminal cysteine. During the assembly process, the cysteine of such internal intermediates, if left free, will react with the C-terminal thioester of the same intermediate molecule or that of a different intermediate molecule, thereby interfering with the desired ligation reaction by the formation of an undesired cyclical peptide or concatemer of the intermediate. This problem can be circumvented by employing a protecting group for the N-terminal cysteine with the following properties: i) it must be stable to the conditions used to cleave the oligopeptide from the synthesis resin, ii) it must be removable after a native chemical ligation has been completed, and iii) preferably, removal takes place in the same ligation reaction mixture before purification, so that the ligation reaction and cysteine deprotection can be conducted in one pot.

SUMMARY OF THE INVENTION

In view of the above, objects of the invention include, but are not limited to, providing a method for convergent synthesis of polypeptides; providing oligopeptide intermediates that can undergo native chemical ligation to form a polypeptide product in a multi-component synthesis, but that are resistant to self-ligation and concatemerization; providing a heterocyclic protecting group for terminal cysteine residues of oligopeptide intermediates of native chemical ligation reactions; providing a method of protecting thioester-modified oligopeptide intermediates from self-ligations or concatemerizations; and providing a method for native chemical ligation of successive oligopeptide intermediates in a single reaction mixture.

The invention accomplishes these and other objectives by providing a thiazolidine protecting group for N-terminal cysteines of internal thioester-modified oligopeptide intermediates of native chemical ligation reactions. Preferably, such protected intermediates are defined by the formula:

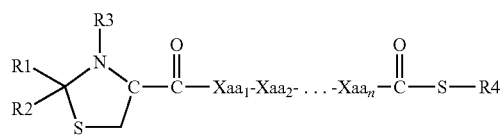

wherein:

Xaa$_i$ is an amino acid for i=1 to n;

n is an integer from 2 to 100, preferably 2 to 70, and more preferably, from 2 to 50;

$R^1$ is selected from H, $C_{1-12}$ (preferably $C_{1-6}$) alkyl groups optionally substituted with 1-3 substituents selected from halo (preferably chloro or bromo), nitro, amino, alkylamino, dialkylamino, amino oxycarbonylamino ($H_2N$—O—$CH_2$—CO—NH—), alkylamino oxycarbonylamino (RHN—O—$CH_2$—CO—NH—), dialkylamino oxycarbonylamino ($R_2N$—O—$CH_2CO$—NH—). Preferably, $R^1$ is selected from the group consisting of H, —$CH_2$—$NO_2$, —$CH_2Cl$, —$CH_2Br$, —$CHCl_2$, —$CHBr_2$;

$R^2$ is selected from H, $C_{1-12}$ (preferably $C_{1-6}$) alkyl groups optionally substituted with 1-3 substituents selected from halo (preferably chloro or bromo), nitro, amino, alkylamino, dialkylamino, amino oxycarbonylamino ($H_2N$—O—$CH_2CO$—NH—), alkylamino oxycarbonylamino (RHN—O—$CH_2CO$—NH—), dialkylamino oxycarbonylamino ($R_2N$—O—$CH_2CO$—NH—). Preferably, $R^2$ is selected from the group consisting of H, $H_2N$—O—$CH_2$—CO—NH—$CH_2$—, $H_2N$—O—$CH_2$—CO—NH—CHCl—, and $H_2N$—O—$CH_2$—CO—NH—CHBr—;

$R^3$ is H or an amino protecting group; and $R^4$ is alkyl having from 1 to 6 carbon atoms or alkylaryl having from 6 to 8 carbon atoms, —$CH_2$—$CONH_2$, —$CH_2CH_2CONH_2$, or —$(CH_2)_k$—CO-Xaa, wherein k is an integer equal to 1 or 2 and Xaa is an amino acid.

Preferably, whenever $R^1$ does not equal $R^2$, the invention includes both chiral variants of the compound. Preferably, whenever $R^3$ is an amino protecting group it is selected from any amino protecting group known to those skilled in the art of peptide synthesis. Preferably, it is selected from the group consisting of tert-butyloxycarbonyl (Boc), (9H-fluoren-9-ylmethoxy)carbonyl (Fmoc), and 2-(4-nitrophenylsulfonyl) ethoxycarbonyl (Nsc).

In accordance with the method of the invention, a polypeptide is synthesized from three or more oligopeptide intermediates by the following steps: (i) forming a ligation product between an oligopeptide possessing both an N-terminal thiazolidine protected cysteine and a C-terminal thioester, and a second oligopeptide possessing an N-terminal cysteine (under conditions which permit the formation of an amide bond between the carboxylic group of the amino acid involved in the thioester linkage and the α-amino group of the N-terminal cysteine of a prior ligation product) (i.e. forming a ligation product with an N-terminal thiazolidine-protected cysteine by reacting an internal oligopeptide intermediate with a prior ligation product under conditions that permit the formation of an amide bond between an α-carbon of a C-terminal thioester amino acid of the internal oligopeptide intermediate and an α-carbon of the N-terminal cysteine of the prior ligation product); (ii) treating the ligation product with a nucleophilic agent under acidic conditions to form a prior ligation product having a free N-terminal cysteine; and (iii) repeating steps d) and e) until the polypeptide is formed.

An important feature of the invention is the deprotection of the N-terminal cysteine by opening the N-terminal thiazolidine ring of the ligation product with a nucleophilic agent under acidic conditions after ligation and in the same reaction mixture. Such agents include, but are not limited to, O-alkylhydroxylamines and hydrazines. Preferably, thiazolidine-protected N-terminal cysteines are deprotected by treatment with an O-alkylhydroxylamine under acidic conditions. More preferably, such O-alkylhydroxylamine deprotection agent has a formula: $H_2N$—O—R, where R is methyl, ethyl, isopropyl, isobutyl, or —$CH_2COOH$. Preferably, R is methyl. Preferably, the acidic conditions include a pH in the range of from 2.0 to 6.0. More preferably, such pH is in the range of from 3.0 to 4.0. Preferably, thiazolidine deprotection is carried out after the amino protecting group has been removed.

The present invention is useful in methods for convergent synthesis of polypeptides and proteins and advantageously addresses limitations in these methodologies. In particular, it provides a method and materials for improving the efficiency of native chemical ligation reactions used to assemble thioester-modified oligopeptide intermediates into polypeptides or proteins, particularly in such reactions involving more than two components.

BRIEF DESCRIPTION OF THE FIGURES

FIG. 2 is a listing of the amino acid sequence (SEQ ID NO: 5) of the polypeptide assembled from four oligopeptide intermediates described in Example 1.

FIG. 4b shows a hypermass reconstructions the raw MS data from the main HPLC peaks of the HPLC chromatograms of FIG. 4a.

FIG. 5a shows analytical HPLC chromatograms of the ligation product of fragment 3 and the ligation product of fragment 1 and fragment 2 before and after thiazolidine deprotection.

FIG. 5b shows a hypermass reconstructions the raw MS data from the main HPLC peaks of the HPLC chromatograms of FIG. 5a.

FIG. 6b shows a hype as reconstructions the raw MS data from the main HPLC peaks of the HPLC chromatograms of FIG. 6a.

FIG. 10 shows the rate of cysteine deprotection for different concentrations of the O-methylhydroxylamine deprotecting agent.

DEFINITIONS

The terms "polypeptide," "peptide," "peptide fragment," "oligopeptide," or "fragment" in reference to a peptide, as used herein refers to a compound made up of a single unbranched chain of amino acid residues linked by peptide bonds. The number of amino acid residues in such compounds varies widely; however, preferably, peptides or oligopeptides referred to herein usually have from 2 to 70 amino acid residues; and more preferably, they have for 2 to 50 amino acid residues. Polypeptides and peptide fragments referred to herein usually have from a few tens of amino acid residues, e.g. 20, to up to a few hundred amino acid residues, e.g. 200, or more.

The term "protein" as used herein may be used synonymously with the term "polypeptide" or may refer to, in addition, a complex of two or more polypeptides which may be linked by bonds other than peptide bonds, for example, such polypeptides making up the protein may be linked by disulfide bonds. The term "protein" may also comprehend a family of polypeptides having identical amino acid sequences but different post-translational modifications, such as phosphorylations, acylations, glycosylations, and the like, particularly as may be added when such proteins are expressed in eukaryotic hosts.

Amino acid residues are referred to herein by their standard single-letter or three-letter notations: A, alanine; C, cysteine; D, aspartic acid; E, glutamic acid; F, phenylalanine; G, glycine; H, histidine; I, Isoleucine; K, lysine; L, leucine; M, methionine; N, asparagine; P, proline; Q, glutamine; R, arginine; S, serine; T, threonine; V, valine; W, tryptophan; Y, tyrosine. An amino acid sequence set forth herein, such as "DKLLM," orders the amino acids from the N-terminus to the C-terminus in a left-to-right manner, unless otherwise indicated from the context.

DETAILED DESCRIPTION OF THE INVENTION

Figure 1:
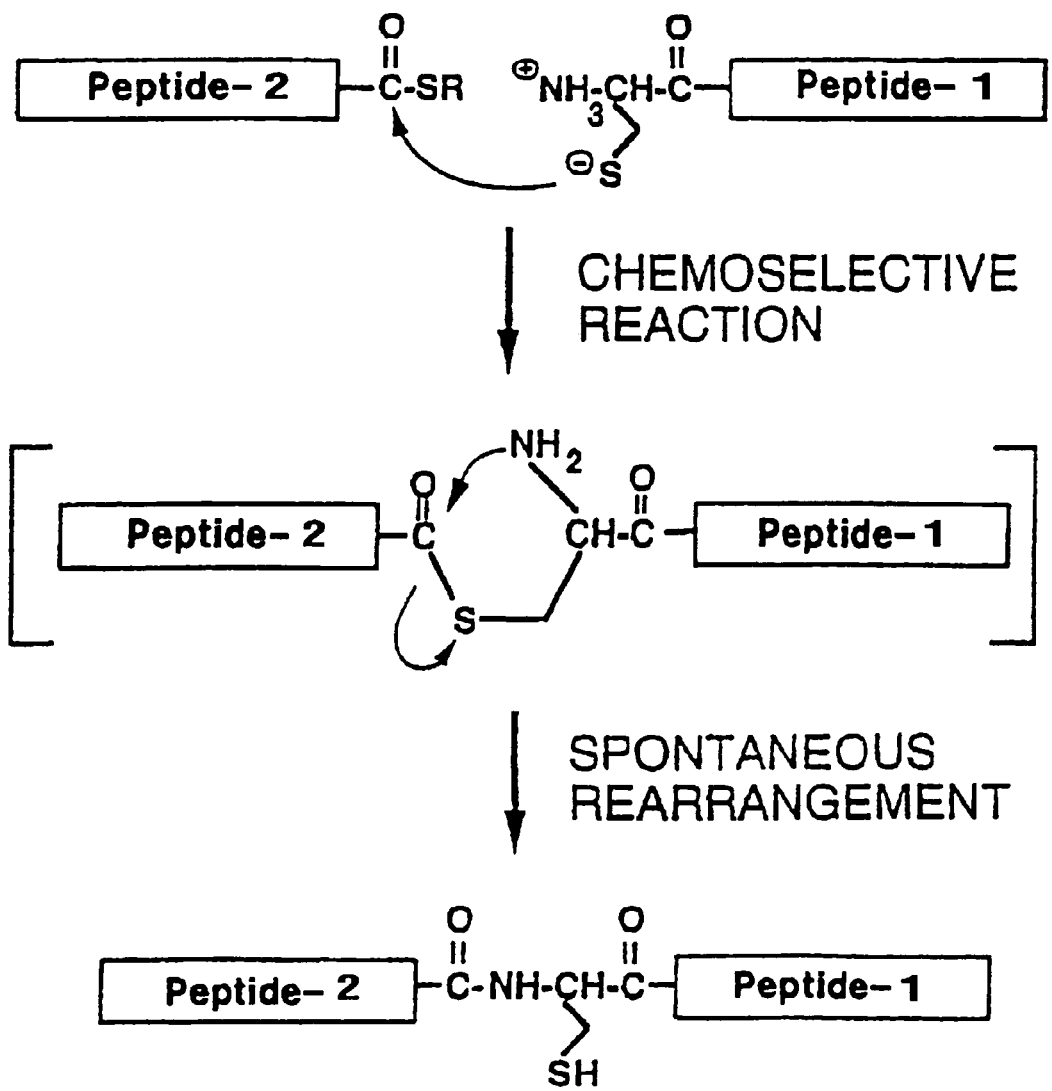
FIG. 1 illustrates the general native chemical ligation scheme related to the invention.

The invention relates to the assembly of oligopeptides into a polypeptide by the process of native chemical ligation, as described by Dawson et al, Science, 266: 776-779 (1994) and Kent et al, U.S. Pat. No. 6,184,344. The general approach of native chemical ligation is illustrated in FIG. 1. A first oligopeptide is provided with an N-terminal cysteine having an unoxidized sulfhydryl side chain, and a second oligopeptide is provided with a C-terminal thioester. The unoxidized sulfhydryl side chain of the N-terminal cysteine is then condensed with the C-terminal thioester to produce an intermediate oligopeptide which links the first and second oligopeptides with a β-aminothioester bond. The β-aminothioester bond of the intermediate oligopeptide then undergoes an intramolecular rearrangement to produce the oligopeptide product which links the first and second oligopeptides with an amide bond.

A problem arises in this scheme when a polypeptide is assembled from three or more fragments. In this situation, at least one fragment will have an N-terminal cysteine and a C-terminal thioester, thereby creating the possibility for self-ligation, which under conventional reaction conditions is quite significant because of the close proximity of the intramolecular reactive moieties. In accordance with the invention, the N-terminal cysteine of an internal fragment is protected from such reactions by a cyclic thiazolidine protecting group. Preferably, such cyclic thiazolidine protecting group is a thioprolinyl group.

Oligopeptides having a C-terminal thioester (Peptide 2 of FIG. 1) may be produced as described in the following references, which are incorporated by reference: Kent et al, U.S. Pat. No. 6,184,344; Tam et al, Proc. Natl. Acad. Sci., 92: 12485-12489 (1995); Blake, Int. J. Peptide Protein Res., 17: 273 (1981); Canne et al, Tetrahedron Letters, 36: 1217-1220 (1995); Hackeng et al, Proc. Natl. Acad. Sci., 94: 7845-7850 (1997); or Hackeng et al, Proc. Natl. Acad. Sci., 96: 10068-10073 (1999); Ingenito et al, J. Am. Chem, Soc., 121: 11369-11374 (1999). Preferably, the method described by Hackeng et al (1999) is employed. Briefly, oligopeptides are synthesized on a solid phase support (described below) typically on a 0.25 mmol scale by using the in situ neutralization/HBTU activation procedure for Boc chemistry disclosed by Schnolzer et al, Int. J. Peptide Protein Res., 40: 180-193 (1992), which reference is incorporated herein by reference. (HBTU is 2-(1H-benzotriazol-1-yl)-1,1,3,3-tetramethyluronium hexafluorophosphate and Boc is tert-butoxycarbonyl). Each synthetic cycle consists of $N^\alpha$-Boc removal by a 1- to 2-minute treatment with neat TFA, a 1-minute DMF flow wash, a 10- to 20-minute coupling time with 1.0 mmol of preactivated Boc-amino acid in the presence of DIEA, and a second DMF flow wash. (TFA is trifluoroacetic acid, DMF is N,N-dimethylformamide, and DIEA is N,N-diisopropylethylamine). $N^\alpha$-Boc-amino acids (1.1 mmol) are preactivated for 3 minutes with 1.0 mmol of HBTU (0.5 M in DMF) in the presence of excess DIEA (3 mmol). After each coupling step, yields are determined by measuring residual free amine with a conventional quantitative ninhydrin assay, e.g. as disclosed in Sarin et al, Anal. Biochem., 117: 147-157 (1981). After coupling of Gln residues, a DCM flow wash is used before and after deprotection by using TFA, to prevent possible high-temperature (TFA/DMF)-catalyzed pyrrolidone formation. After chain assembly is completed, the oligopeptides are deprotected and cleaved from the resin by treatment with anhydrous HF for 1 hour at 0° C. with 4% p-cresol as a scavenger. The imidazole side-chain 2,4-dinitrophenyl (dnp) protecting groups remain on the His residues because the dnp-removal procedure is incompatible with C-terminal thioester groups. However, dnp is gradually removed by thiols during the ligation reaction. After cleavage, oligopeptides are precipitated with ice-cold diethylether, dissolved in aqueous acetonitrile, and lyophilized.

Preferably, the protecting group of the invention is incorporated in the thioester oligopeptide by coupling a N-protected 2-substituted thiazolidine-4-carboxilic acid in the last synthesis cycle. Preferably, such N-protected 2-substituted thiazolidine-carboxilic acid has the formula:

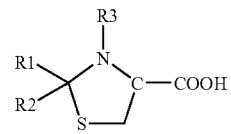

where $R^1$ is selected from the group consisting of H, —$CH_2NO_2$, —$CH_2Cl$, —$CH_2Br$, —$CHCl_2$, —$CHBr_2$; $R^2$ is selected from the group consisting of H, $H_2N$—O—$CH_2$—CO—NH—$CH_2$—, $H_2N$—O—$CH_2$—CO—NH—CHCl—, and $H_2N$—O—$CH_2$—CO—NH—CHBr—; and where $R^3$ is an amino protecting group. Preferably, $R^3$ is Boc, Fmoc, or Nsc.

More preferably, the N-protected thiazolidine-4-carboxilic acid is an N-protected thioproline of the formula:

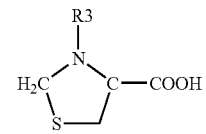

wherein $R^3$ is Boc or Fmoc. Most preferably, $R^3$ is Boc.

Thioester oligopeptides may be synthesized using either Fmoc or Boc chemistries. When Fmoc chemistry is employed a 3-carboxypropanesulfonamide safety catch linker is used to generate the thioester. Thioester oligopeptides described above are preferably synthesized on a trityl-associated mercaptopropionic acid-leucine (TAMPAL) resin, made as disclosed by Hackeng et al (1999), or comparable protocol. Briefly, $N^\alpha$-Boc-Leu (4 mmol) is activated with 3.6 mmol of HBTU in the presence of 6 mmol of DIEA and coupled for 16 minutes to 2 mmol of p-methylbenzhydrylamine (MBHA) resin, or the equivalent. Next, 3 mmol of S-trityl mercaptopropionic acid is activated with 2.7 mmol of HBTU in the presence of 6 mmol of DIEA and coupled for 16 minutes to Leu-MBHA resin. The resulting TAMPAL resin can be used as a starting resin for polypeptide-chain assembly after removal of the trityl protecting group with two 1-minute treatments with 3.5% triisopropylsilane and 2.5% $H_2O$ in TFA. The thioester bond can be formed with any desired amino acid by using standard in situ-neutralization peptide coupling protocols for 1 hour, as disclosed in Schnolzer et al (cited above). Treatment of the final oligopeptide with anhydrous HF yields the C-terminal activated mercaptopropionic acid-leucine (MPAL) thioester oligopeptides.

Preferably, thiazolidine-protected thioester oligopeptide intermediates are used in native chemical ligation under conditions as described by Hackeng et al (1999), or like conditions. Briefly, 0.1 M phosphate buffer (pH 8.5) containing 6 M guanidine, 2% (vol/vol) benzylmercaptan, and 2% (vol/vol)

thiophenol is added to dry peptides to be ligated, to give a final peptide concentration of 1-3 mM at about pH 7, lowered because of the addition of thiols and TFA from the lyophilized peptide. Preferably, the ligation reaction is performed in a heating chamber at 37° C. under continuous stirring and is periodically vortexed to equilibrate the thiol additives. The reaction may be monitored for degree of completion by MALDI-MS or HPLC and electrospray ionization MS.

After a native chemical ligation reaction is completed or stopped, the N-terminal thiazolidine ring of the product is opened by treatment with a thiazolidine deprotecting agent. A thiazolidine deprotecting agent is nucleophilic under acidic conditions, such as certain O-alkylhydroxylamines, hydrazines, or like reagents. Preferably, the N-terminal thiazolidine ring of the product is opened by treatment with O-methylhydroxylamine (0.5 M) at pH 3.5-4.5 for 2 hours at 37° C. after which a 10-fold excess of Tris-(2-carboxyethyl)-phosphine (TCEP) is added to the reaction mixture to completely reduce any oxidizing reaction constituents prior to purification of the product by conventional preparative HPLC. Preferably, fractions containing the ligation product are identified by electrospray MS, are pooled, and lyophilized. Other reducing agents that can be used in place of Tris-(2-carboxyethyl)-phosphine include β-mercaptoethanolamine, dithiotreitol, and the like.

Deprotecting the cysteine of the final product is an important feature of the invention and may be accomplished with a variety of agents that are nucleophilic under acidic conditions, as mentioned above. Opening the thiazolidine ring under acidic conditions depends on its C2 substituents (Wohr et al, J. Am. Chem. Soc., 118: 9218 (1994)). The following compounds may be used as thiazolidine deprotecting agents: O-methylhydroxylamine and other hydroxylamine derivatives, which are nucleophiles under acidic conditions, permit formation of an oxime and displacement of the equilibrium towards the unprotected form of N-terminal Cys. Hydrazine or any of its derivatives, as well as thiosemicarbazides, which are nucleophilic under acidic conditions, may also be used, but this family of reagents is more toxic than the former one and the condensation product (hydrazone, thiosemicarbazone, respectively) is less stable than the oxime. Preferably, Tris-2-carboxyethyl)-phosphine (TCEP), or like reducing agent, is used in the deprotection reaction to rapidly and stochiometrically reduces most peptides and sulfhydryls even under acidic conditions (Burns et al., J. Org. Chem., 56: 2648-2650, 1991). Preferably, O-methylhydroxylamine is used as the thiazolidine deprotecting agent. O-methylhydroxylamine reacts with the masked aldehyde function in the thiazolidine ring to form an oxime, as shown below.

After the synthesis is completed and the final product purified, the final polypeptide product may be refolded by conventional techniques, e.g. Creighton, Meth. Enzymol., 107: 305-329 (1984); White, Meth. Enzymol., 11: 481-484 (1967); Wetlaufer, Meth. Enzymol., 107: 301-304 (1984); Misawa et al, Biopolymers, 51: 297-307 (1999); Anfinsen, Science, 181: 223-230 (1973); and the like. Preferably, a final product is refolded by air oxidation by the following, or like: The reduced lyophilized product is dissolved (at about 0.1 mg/mL) in 1 M guanidine hydrochloride (or like chaotropic agent) with 100 mM Tris, 10 mM methionine, at pH 8.6. After gentle overnight stirring, the re-folded product is isolated by reverse phase HPLC with conventional protocols.

In a further aspect of the present invention there is provided a method of synthesizing a polypeptide by ligation of three or more oligopeptide intermediates, the method comprising the steps of:

a) providing an initial oligopeptide intermediate having an N-terminal cysteine with an α-carbon;

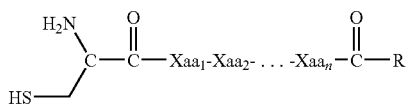

wherein:

Xaa$_i$ is an amino acid for i=1 to n;

n is an integer from 2 to 100, preferably 2 to 70; and

R is either —OH or —NH$_2$;

b) providing one or more internal oligopeptide intermediates each having a C-terminal amino acid thioester and an N-terminal thiazolidine-protected cysteine, the oligopeptide intermediate initially having the formula:

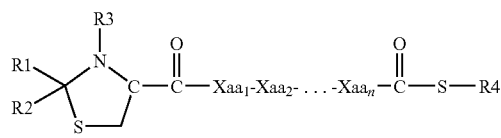

wherein:

Xaa$_i$, n, and R$^4$ are defined as above;

n is an integer from 2 to 100, preferably 2 to 70;

R$^1$ and R$^2$ are hydrogen;

R$^3$ is hydrogen or an amino protecting group selected from the group consisting of Boc and Fmoc;

c) providing a terminal oligopeptide intermediate having a C-terminal amino acid thioester and, whenever such terminal

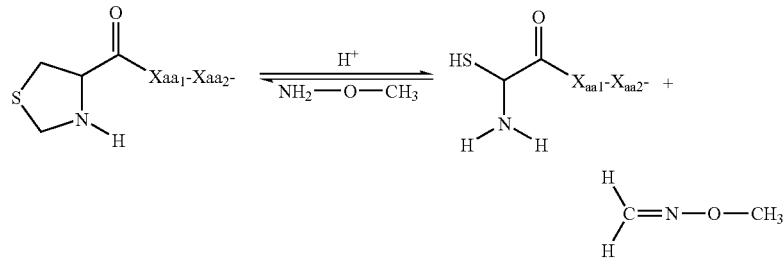

oligopeptide intermediate has an N-terminal cysteine, an N-terminal thiazolidine-protected cysteine;

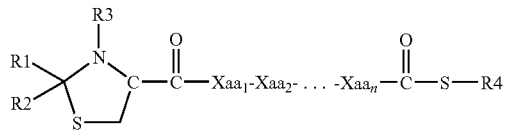

wherein $Xaa_i$, n, $R^1$, $R^2$, $R^3$, and $R^4$ are defined as above (in a preferred embodiment, $R^1$=$R^2$=$R^3$=H although it will be appreciated that according to the synthesis procedure $R^3$ will be a protecting group such as Boc or Fmoc, but for the cleavage from the resin, which means $R^4$ no longer attached to the linker of the solid phase support, the secondary amine will be deprotected);

d) forming a ligation product with an N-terminal thiazolidine-protected cysteine by reacting an internal oligopeptide intermediate with the initial oligopeptide intermediate or a prior ligation product having an N-terminal cysteine with a free α-amine under conditions that permit the formation of an amide bond between the carboxylic group of the C-terminal thioester amino acid of the internal oligopeptide intermediate and the free α-amine of the N-terminal cysteine of the prior ligation product or the initial oligopeptide intermediate;

e) treating the ligation product with an O-alkylhydroxylamine under acidic conditions in the range of from pH 2.0 to 6.0 to form a prior ligation product having a free N-terminal cysteine;

f) repeating steps d) and e) until all of the internal oligopeptide intermediates are ligated; and g) forming the polypeptide by reacting the terminal oligopeptide intermediate with the prior ligation product under conditions that permit the formation of an amide bond between the α-amine of the N-terminal cysteine of the prior ligation product and the carboxylic group of the amino acid involved in the thioester linkage of the N-terminal oligopeptide intermediate.

EXAMPLE 1

In this example, a polypeptide having the sequence of FIG. 2 (SEQ ID NO: 5) was synthesized with the method and materials of the invention. The full length polypeptide was assembled from the previously synthesized oligopeptide intermediates listed below (the superscripted numbers indicate the position of the fragments in the sequence of FIG. 2). Fragment 1 was initially coupled to fragment 2 to give a first product, then after preparative HPLC purification, the first product was coupled to fragment 3 to give a second product. Again, after preparative HPLC purification, the second product was coupled to fragment 4 to give the desired polypeptide, which was purified and refolded.

Thioester formation. Fragments 2, 3, 4 were synthesized on a thioester generating resin. For this purpose S-acetylthioglycolic acid pentafluorophenylester was coupled to a Leu-PAM resin under conditions essentially as described by Hackeng et al (1999). The resulting resin was used as a starting resin for peptide chain elongation on a 0.2 mmol scale after removal of the acetyl protecting group with a 30 min treatment with 2M mercaptoethanol, 2M piperidine in DMF. The thioester was formed with Boc-Gly-OH for synthesis of fragment 2, Boc-Ile-OH for fragment 3 and Boc-Phe-OH for fragment 4 using the standard in situ neutralization coupling protocol for 1 hour, Schnölzer et al (cited above), with a 4-fold molar excess of aa over the sulfhydryl group. The $N^α$ of the N-terminal Cys residues of fragments 2 and 3 were protected in accordance with the invention by coupling a Boc-thioproline (Boc-SPr, i.e. Boc-L-thioproline) to the terminus of the respective chains instead of a Cys having conventional $N^α$ or $S^β$ protection, e.g. Brik et al, J. Org. Chem., 65: 3829-3835 (2000)

Figure 3:
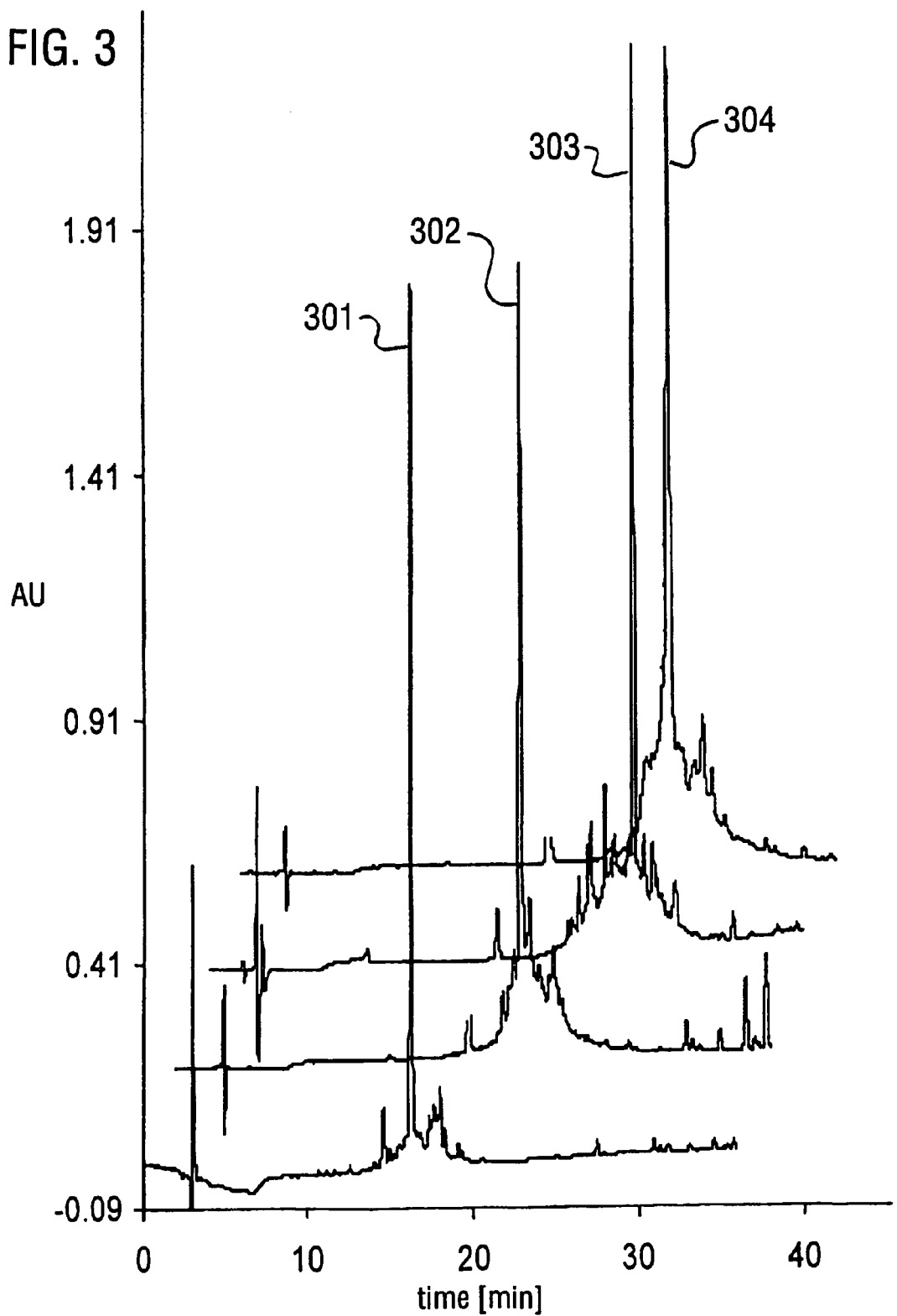
FIG. 3 shows analytical HPLC chromatograms of the crude peptides of Example 1: fragment 1 (301; SEQ ID NO: 1), fragment 2 (302; SEQ ID NO: 2), fragment 3 (303; SEQ ID NO: 3), and fragment 4 (304; SEQ ID NO: 4).

Peptide synthesis. Solid-phase synthesis was performed on a custom-modified 433A peptide synthesizer from Applied Biosystems, using in situ neutralization/2-1H-benzotriazol-1-yl)-1,1,1,3,3-tetramethyluronium hexafluoro-phosphate (HBTU) activation protocols for stepwise Boc chemistry chain-elongation, as described by Schnolzer et al, Int. J. Peptide Protein Res., 40: 180-193 (1992). Each synthetic cycle consisted of $N^α$-Boc-removal by a 1 to 2 min treatment with neat TFA, a 1-min DMF flow wash, a 10-min coupling time with 2.0 mmol of preactivated Boc-amino acid in the presence of excess DIEA and a second DMF flow wash. Nα-Boc-amino acids (2 mmol) were preactivated for 3 min with 1.8 mmol HBTU (0.5M in DMF) in the presence of excess DIEA (6 mmol). After coupling of Gln residues, a dichloromethane flow wash was used before and after deprotection using TFA, to prevent possible high temperature (TFA/DMF)-catalyzed pyrrolidone carboxylic acid formation. Side-chain protected amino acids were Boc-Arg(p-toluenesulfonyl)-OH, Boc-Asn (xanthyl)-OH, Boc-Asp(O-cyclohexyl)-OH, Boc-Cys(4-methylbenzyl)-OH, Boc-Glu(O-cyclohexyl)-OH, Boc-His(dinitrophenylbenzyl)-OH, Boc-Lys(2-Cl—Z)—OH, Boc-Ser (benzyl)-OH, Boc-Thr(benzyl)-OH, Boc-Trp(formyl)-OH and Boc-Tyr(2-Br—Z)—OH (Orpegen Pharma, Heidelberg, Germany). Other amino acids were used without side chain protection. C-terminal Fragment 1 was synthesized on Boc-Leu-O—$CH_2$-Pam resin (0.7 mmol/g of loaded resin), while for Fragments 2, 3 and 4 machine-assisted synthesis was started on the Boc-Xaa-S—$CH_2$—CO-Leu-Pam resin. FIG. 3 shows analytical HPLC chromatograms of the crude peptides of fragment 1 (301), fragment 2 (302), fragment 3 (303), and fragment 4 (304).

After chain assembly was completed, the peptides were deprotected and cleaved from the resin by treatment with anhydrous hydrogen fluoride for 1 hr at 0° C. with 5% p-cresol as a scavenger. In all cases except Fragment 1, the imidazole side chain 2,4-dinitrophenyl (DNP) protecting groups remained on His residues because the DNP-removal

| Fragment | SEQ ID NO | Sequence of Oligopeptide Intermediate |
|---|---|---|
| 1 | 1 | $C^{130}$AEKSDYIRK INELMPKYAP KAASARTDL$^{158}$ |
| 2 | 2 | $C^{82}$EKLKKKDSQ ICELKYDKQI DLSTVDLKKL RVKELKKILD DWGETCKG$^{129}$ |
| 3 | 3 | $C^{40}$REARGKENR LCYYIGATDD AATKIINEVS KPLAHHIPVE KI$^{81}$ |
| 4 | 4 | $L^1$RPGDCEVCI SYLGRFYQDL KDRDVTFSPA TIENELIKF$^{39}$ | procedure is incompatible with C-terminal thioester groups. However DNP is gradually removed by thiols during the ligation reaction, yielding unprotected His. After cleavage, both peptides were precipitated with ice-cold diethylether, dissolved in aqueous acetonitrile containing 0.1% TPA and lyophilized. The peptides were purified by RP-HPLC with a C18 column from Waters by using linear gradients of buffer B (acetonitile/0.1% trifluoroacetic acid) in buffer A (H$_2$O/0.1% trifluoroacetic acid) and UV detection at 214 nm. Collected fractions were analyzed by electrospray mass spectrometry (ESMS) using an Esquire instrument (Brücker, Bremen, Germany) and by analytical HPLC. Fractions containing the right product were pooled and freeze-dried.

Native chemical ligations. As described more fully below, the ligation of unprotected fragments was performed as follows: the dry peptides were dissolved in equimolar amounts in 6M guanidine hydrochloride (GuHCl), 0.2M phosphate, pH 7.5 in order to get a final peptide concentration of 1-5 mM at a pH around 7, and 2% thiophenol was added. Usually, the reaction was carried out overnight and was monitored by HPLC and electrospray mass spectrometry. The ligation product was subsequently treated to hydrolyze any remaining thioester and to remove protecting groups still present. For this purpose and in order to remove the formyl group of Trp, 20%2-mercaptoethanol was added and the pH shifted to 9.0 by addition of hydrazine and the solution incubated for 1 h at 37° C. The reaction mixture was then acidified to pH 3.5 with 6M HCl and 2M O-methylhydroxylamine in 6M guanidine-hydrochloride, pH3.5 added to get a final 0.5M concentration. A 2 h incubation at 37° C. is required for complete opening of the N-terminal thiazolidine ring. A 10-fold excess of Tris(2-carboxyethyl)phosphine over the fragment was added and the material purified by preparative HPLC after 15 min incubation. Fractions containing the polypeptide chain were identified by ESMS, pooled and lyophilized.

Figure 4A:
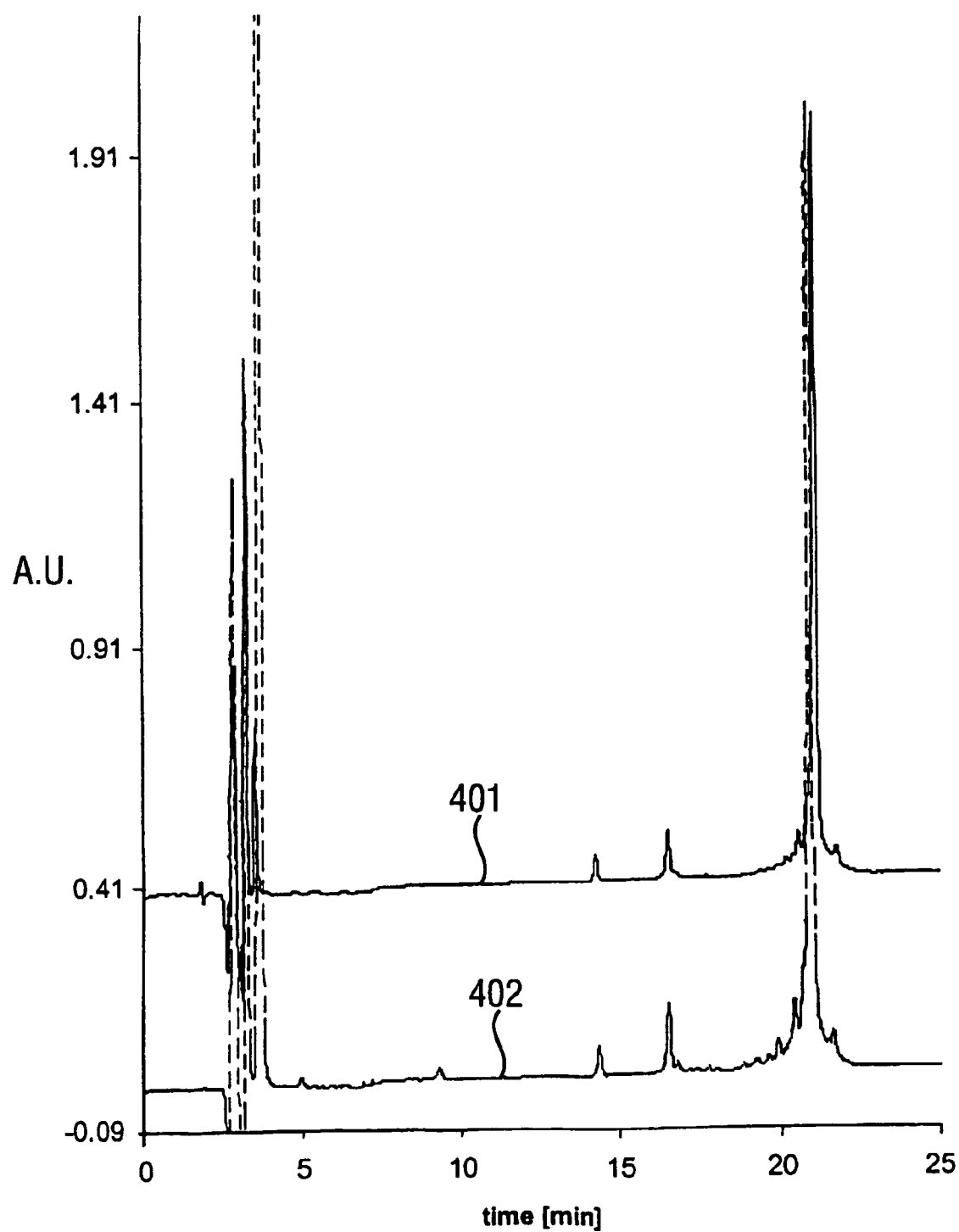
FIG. 4a shows analytical HPLC chromatograms of the ligation product of fragment 1 and fragment 2 before and after thiazolidine deprotection.
Figure 4B:
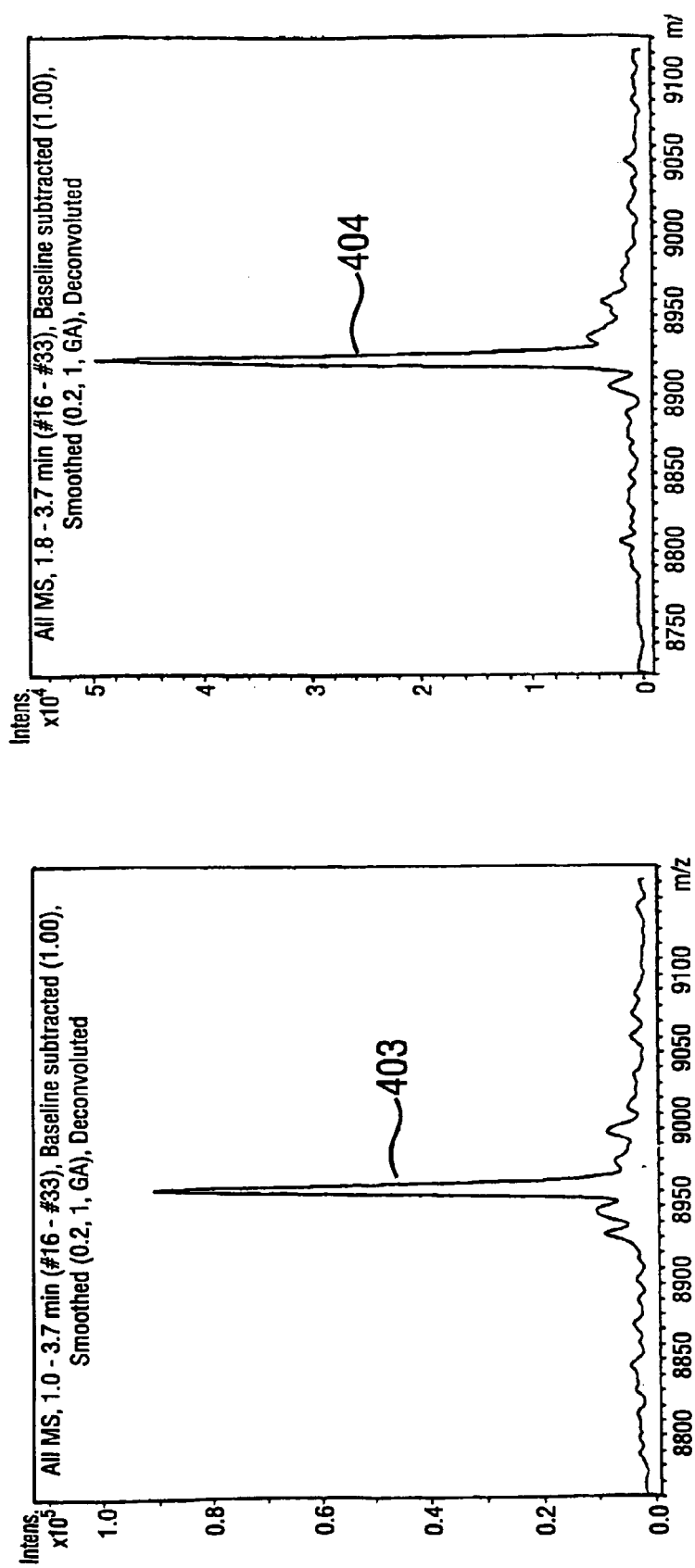

The ligation of SPr$^{82}$-(82-129)-αCOSR (fragment 2) and Cys$^{130}$(130-158)-COOH (fragment 1) peptides was performed at pH7.0 in 6 M GuHCl. The concentration of each reactant was 5 mM, and 2% thiophenol were added to create a reducing environment and facilitate the ligation reaction. An almost quantitative ligation reaction is observed after overnight stirring at 37° C. ESMS confirmed the molecular mass for the SPr$^{82}$-(82-158)-COOH polypeptide chain of 8960.8 Da, in good agreement with the calculated average isotopic mass of 8960.5 Da. At this point in the reaction, 2-mercaptoethanol was added to a 20%(v/v) final concentration and hydrazine added to shift the pH to 9.0, for the removal of the formyl group of Trp$^{123}$. After a 1 h incubation at 37° C., the medium was acidified, CH$_3$—O—NH$_2$.HCl was added to the solution to give a 0.5M final concentration, and the pH adjusted to 3.5 in order to open the thiazolidine ring of SPr$^{82}$. After 2 h incubation at 37° C., ESMS confirmed the removal of the two protecting groups (Table 1), corresponding to the loss of 28 and 12 Da, respectively. The reaction mixture was subsequently treated with a 10-fold excess of Tris(2-carboxyethylphosphine) over the peptide and after 15 min, the ligation product was purified using the preparative HPLC (C4, 20-60% CH$_3$CN, 0.5% per min and a flow rate of 20 mL/min), lyophilised and stored at −20° C. FIG. 4a shows analytical HPLC chromatograms of the ligation product of fragment 1 and fragment 2 where curve (401) is the chromatogram of the product before thiazolidine deprotection and curve (402) is the chromatogram of the product after thiazolidine deprotection. FIG. 4b shows a hypermass reconstructions the raw MS data from the main HPLC peaks of the HPLC chromatograms of FIG. 4a, wherein curve (403) corresponds to the peak of curve (401) (closed thiazolidine ring) and curve (404) corresponds to the peak of curve (402) (open thiazolidine ring).

Figure 5B:
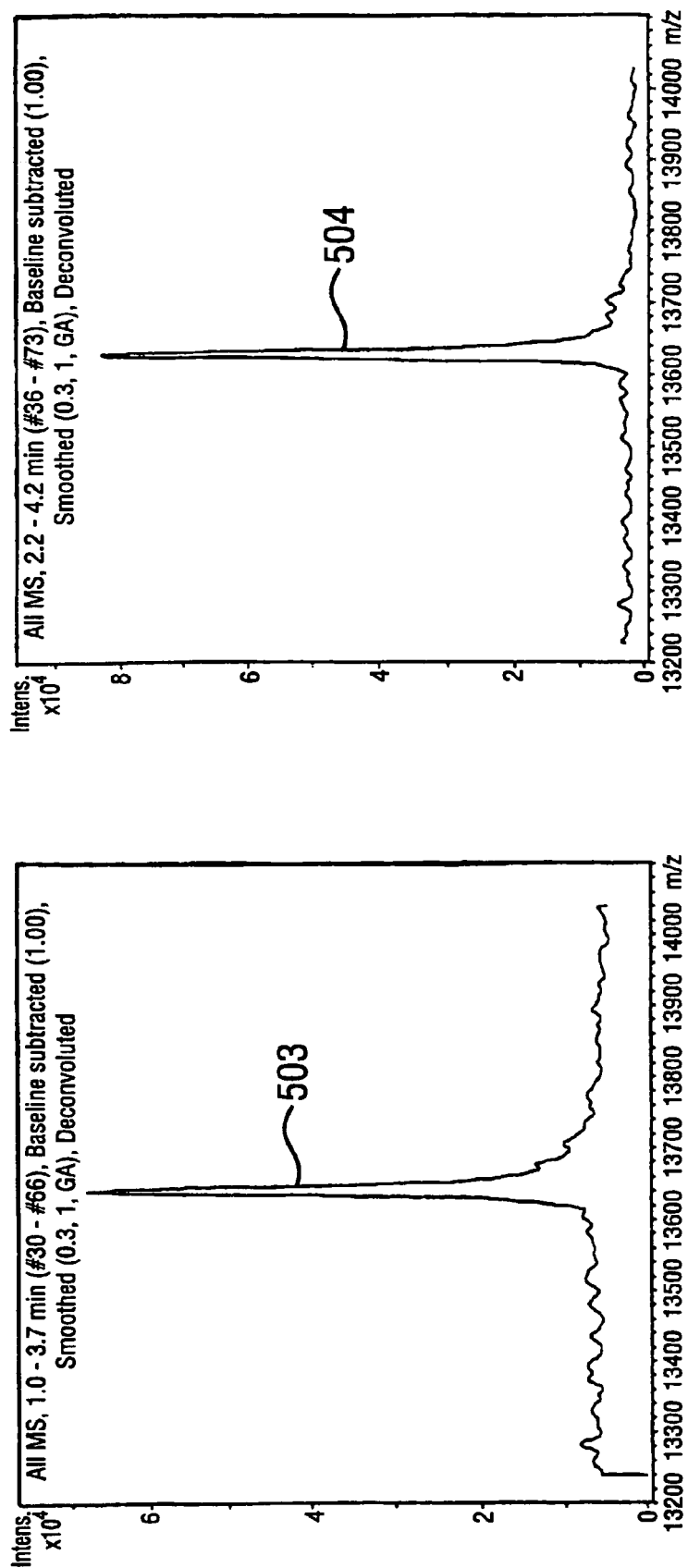

The same procedure was repeated for ligation 2 with some slight modifications. Since ligation reaction 2 involves an Ile-Cys ligation site, which is one of the less favourable ones according to a comparative study (Hackeng et al, P.N.A.S., 96, 10068-10073, 1999), the ligation reaction was carried over 48 h. According to the HPLC profile, only a 60% ligation yield could be obtained after 48 h incubation. FIG. 5a shows analytical HPLC chromatograms of the ligation product of the above ligation product and fragment 3 where curve (501) is the chromatogram of the product before thiazolidine deprotection and curve (502) is the chromatogram of the product after thiazolidine deprotection. FIG. 5b shows a hypermass reconstruction the raw MS data from the main HPLC peaks of the HPLC chromatograms of FIG. 5a, wherein curve (503) corresponds to the peak of curve (501) (closed thiazolidine ring) and curve (504) corresponds to the peak of curve (502) (open thiazolidine ring).

Figure 6A:
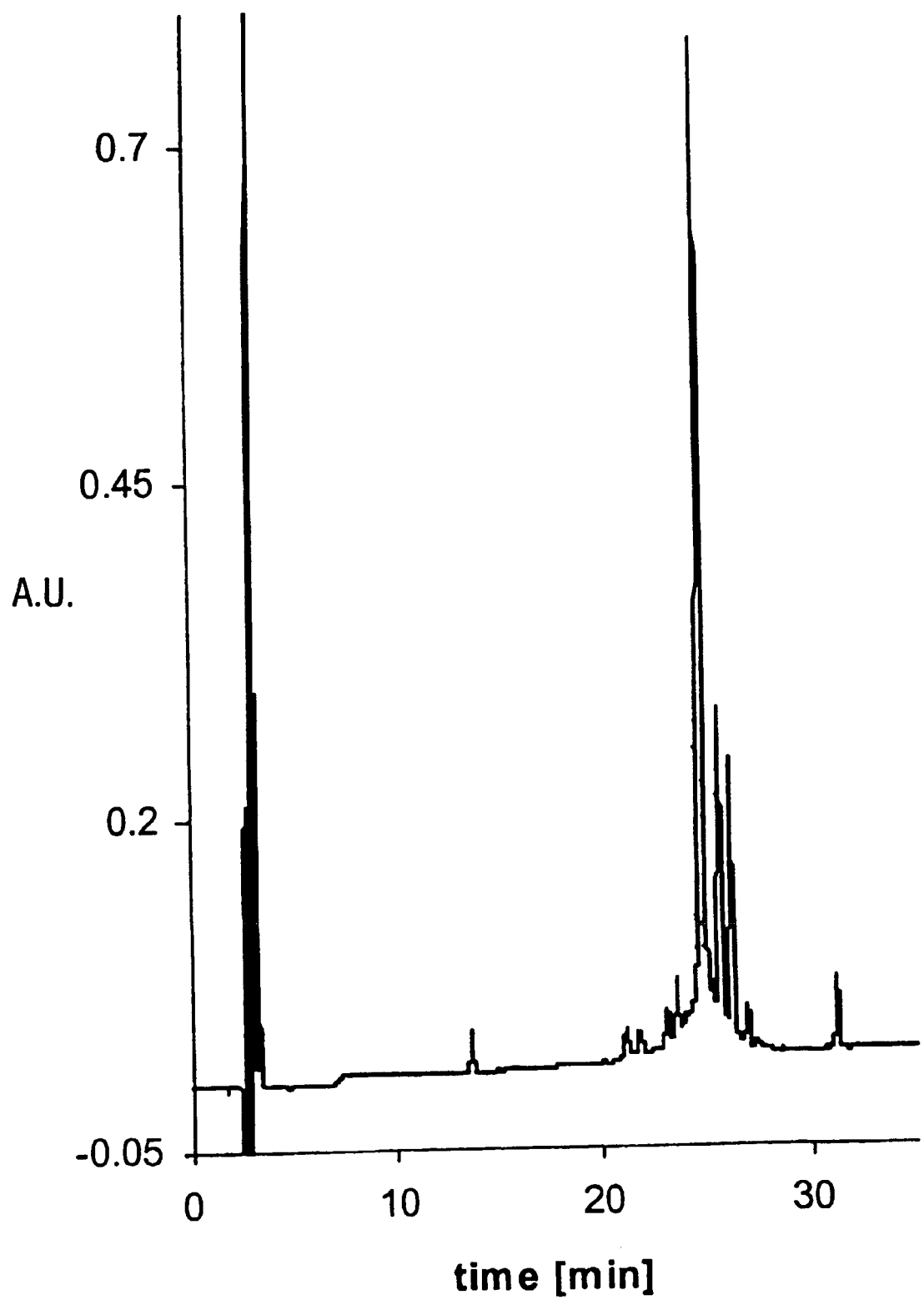
FIG. 6a shows an analytical HPLC chromatogram of the final ligation product of fragments 1, 2, 3, and 4.
Figure 6B:
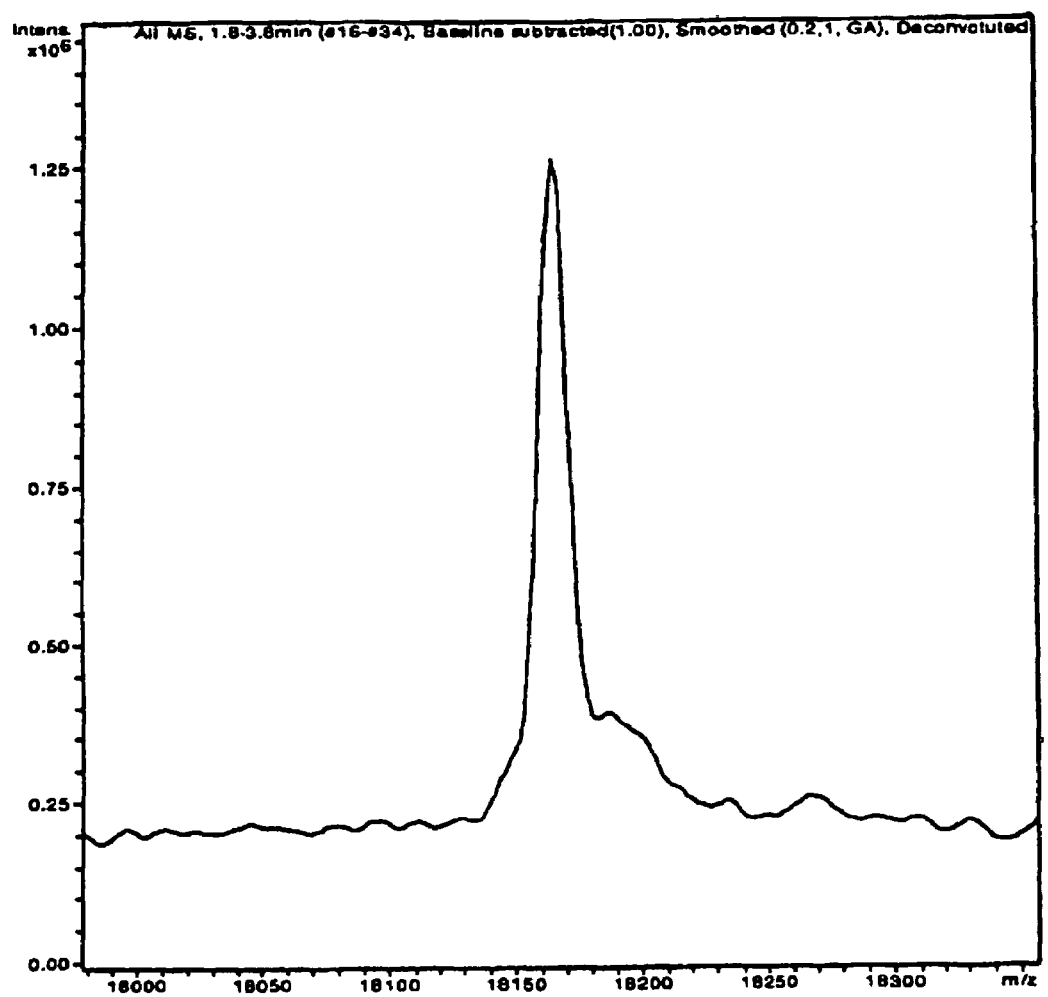
Figure 7:
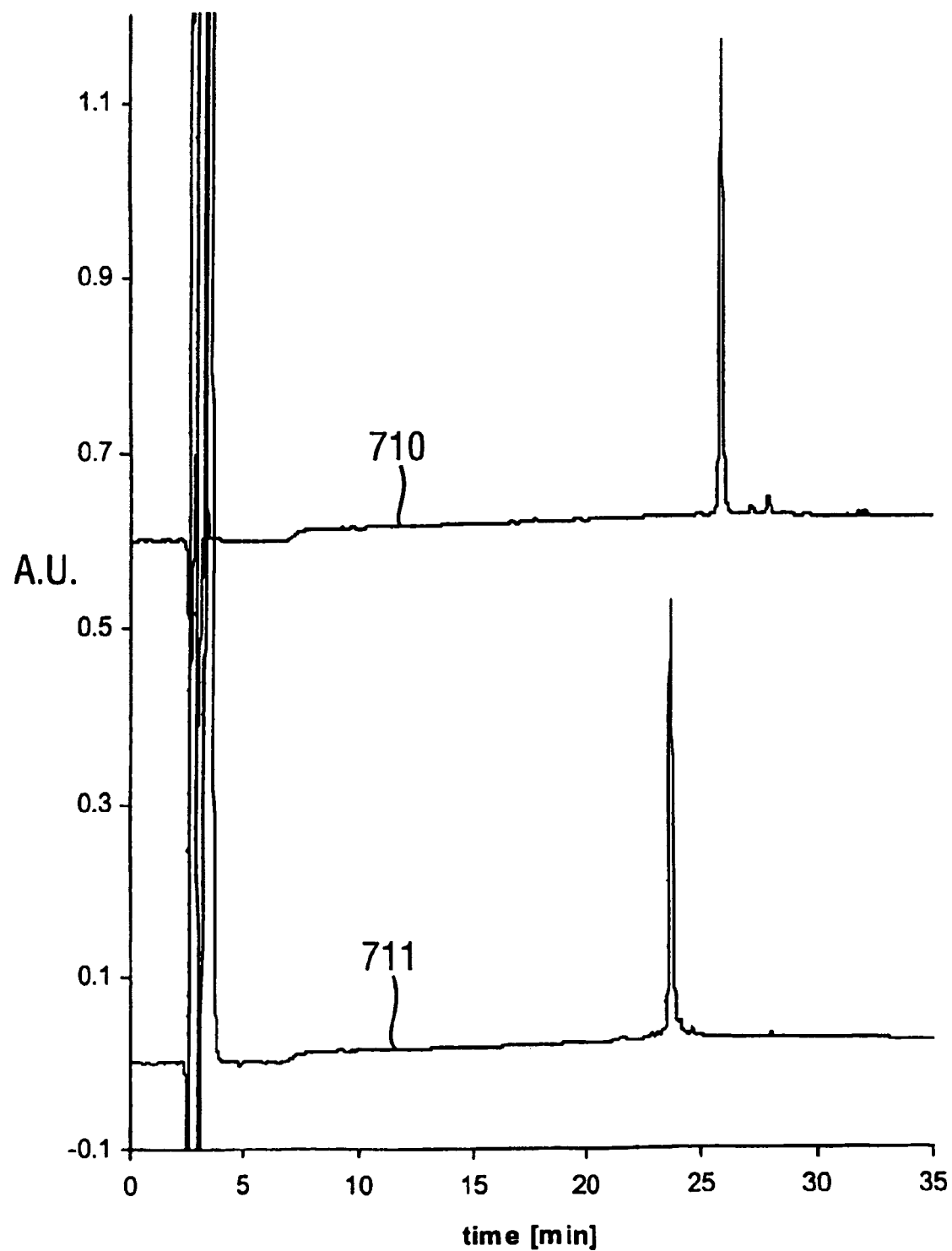
FIG. 7 shows analytic HPLC chromatograms of the purified and reduced final ligation product and the crude folded material.
Figure 8:
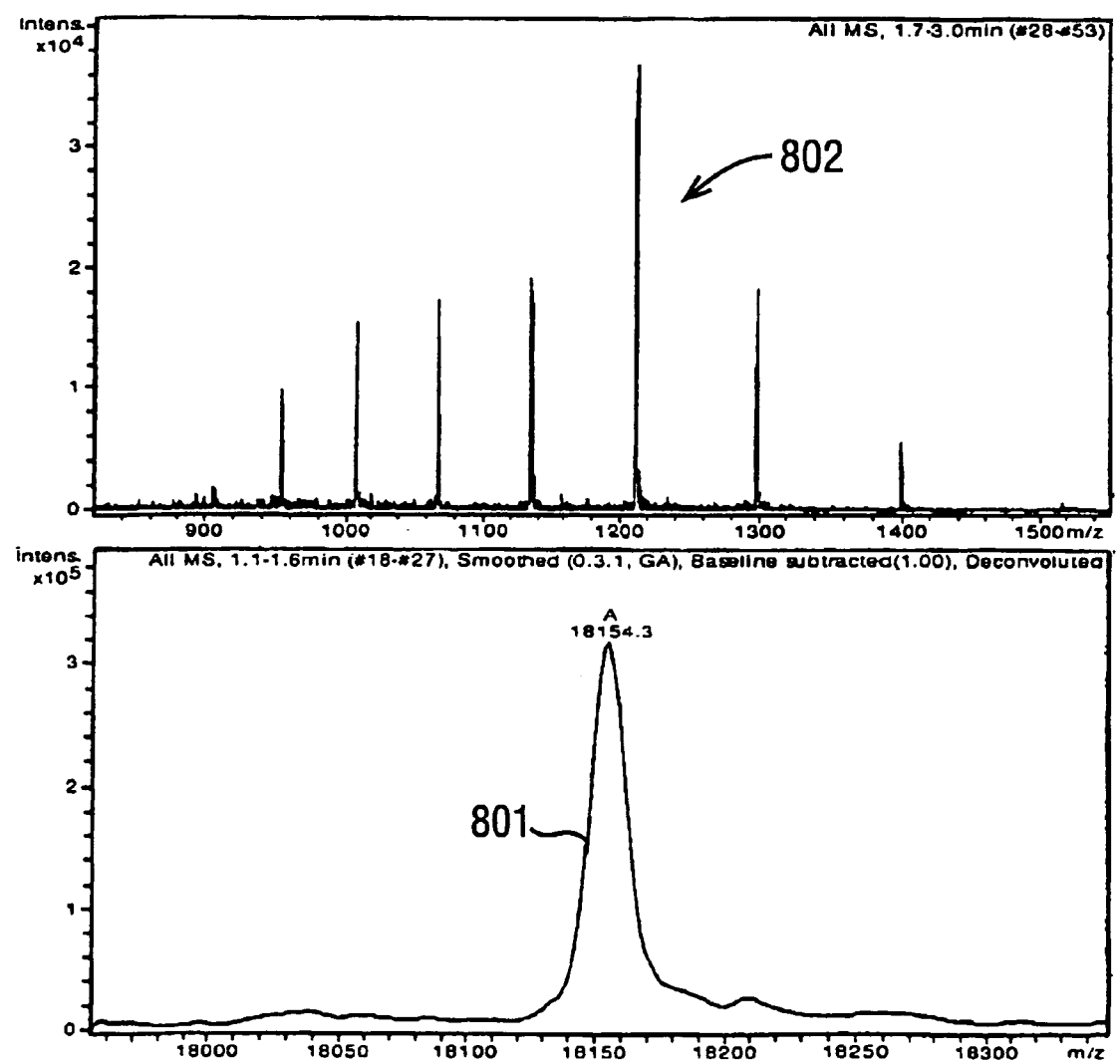
FIG. 8 shows a hypermass reconstruction and the raw MS data from the main HPLC peak of the final folded material of FIG. 7.

Ligation 3 didn't require any further work-up of the full length peptide: the ligation medium was immediately purified after acidification and TCEP treatment. FIG. 6a shows an analytical HPLC chromatogram of the final ligation product of fragments 1, 2, 3, and 4. FIG. 6b shows a hypermass reconstruction of the raw MS data from the main peak of the chromatogram of FIG. 6a. FIG. 7 shows analytic HPLC chromatograms of the purified and reduced final ligation product (710) and the crude folded material (711). FIG. 8 shows a hypermass reconstruction (801) and the raw MS data (802) from the main HPLC peak of the final folded material of FIG. 7 curve (711).

Polypeptide Folding. The full length peptide was refolded by dissolving the reduced lyophilized protein (about 0.1 mg/mL) in 1M GuHCl, 100 mM Tris, 0.5 mM reduced glutathione, 0.1 mM oxidized glutathione 10 mM methionine, pH 8.6 After gentle stirring overnight, the protein solution was purified by RP-HPLC as described above. The masses of the reduced and refolded proteins agreed well with their calculated average isotopic mass as summarized in Table 1.

TABLE I

ESMS Characterization of Oligopeptide Intermediates in the Synthesis of Full Length Product, Gln$^1$-Leu$^{161}$

| Fragment | Calculated Mass (Daltans, average isotope) | Measured Mass (Daltons, average isotope) |
| --- | --- | --- |
| (Cys$^{130}$-Leu$^{158}$,)-COOH | 3283.2 | 3283.2 |
| (SPr$^{82}$-Gly$^{124}$, Trp$^{124}$(CHO))-αCOSR | 5882.0 | 5882.3 |
| (SPr$^{40}$-Ile$^{81}$, His$^{74,75}$ (DNP))-αCOSR | 5255.95 | 5256.1 |
| (Leu$^1$-Phe$^{39}$)-αCOSR | 4740.49 | 4739.5 |
| Ligation 1 product Cys$^{82}$-(82-158)-COOH | 8920.54 | 8920.0 |
| Ligation 2 product Cys$^{40}$-(40-158)-COOH | 13626.99 | 13627.8 |
| Ligation 3 product Leu$^1$-(1-158)-COOH | 18162.19 | 18163.5 |
| Refolded Leu$^1$(1-158)-COOH | 18154.19 | 18154.3 |

EXAMPLE 2

A polypeptide with the sequence CYAKYAKL (SEQ ID NO: 6) was synthesized using in situ neutralization/2-(1H-benzotriazol-1yl)-1,1,1,3,3-tetrametyluronium hexafluorophosphate (HBTU) activation protocol for stepwise Boc chemistry as previously described (see example 1). The N-terminal cysteine was introduced as Boc-Thioproline, with standard HBTU activation. After Boc removal the peptide was cleaved from the resin by treatment with hydrogen fluoride for 1 hr at 0° with 5% p-cresol as scavenger. The purified final product presented the expected mass of 970.18, consistent with a stable thioproline N-terminal cysteine, confirming the stability of the thioproline ring in the cleavage conditions.

A series of experiments to determine the optimal conditions for thiazolidine ring opening were conducted at different pH and different O-methylhydroxylamine concentrations. The extent of ring opening was calculated by analytical RP-HPLC. The ring opening induced a net shift in elution time that allows the complete resolution of the two peptides. MS analysis of the products confirmed a loss of 12 amu, consistent with the formation of a free cysteine at the N-terminus of the peptide.

Figure 9:
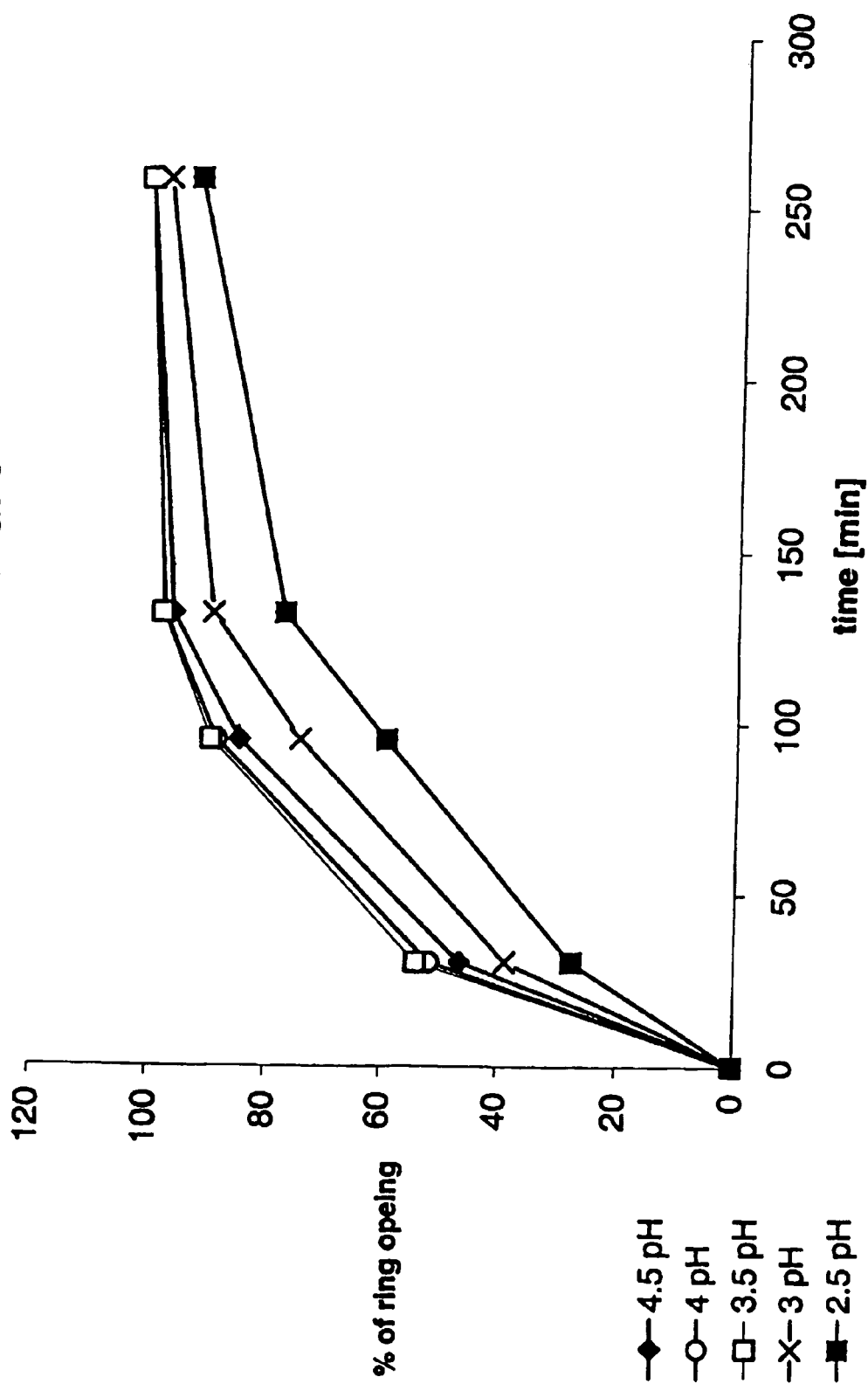
FIG. 9 shows the rate of cysteine deprotection for different pH conditions.

Optimal pH assay: Aliquots of 100 μg of peptide were dissolved in a solution 6 M Guanidine hydrorchloride, 0.5 M O-methylhydroxylamine, corrected either at pH 4.5, or pH 4.0, or pH 3.5, or pH 3.0 and pH 2.5. Samples of the reaction media were analyzed at time 30, 90, 130, and 250 minutes. Peaks corresponding to SPrYAKYAKL (SEQ ID NO: 7) and CYAKYAKL (SEQ ID NO: 6) were integrated and the extent of ring opening calculated based on the % of the CYAKYAKL (SEQ ID NO: 6) peak. As evident from FIG. 9, the optimal conditions for conversion of thioproline to cysteine are at pH 3.5, or higher. At pH lower than 3.5, the reaction becomes slower, which is possibly related to the pKa of the nitrogen of the O-methylhydroxylamine.

O-methylhydroxylamine optimal concentration assay. Aliquots of 100 μg of peptide were dissolved in a solution 6 M Guanidine hydrorchloride with either 0.5 M O-methylhydroxylamine, or 0.25 M O-methylhydroxylamine, or 0.125 M O-methylhydroxylamine or 0.0625 M O-methylhydroxylamine, all adjusted to pH 3.5. Samples of the reaction media were analyzed at the following times: 30, 90, 130, 250 minutes. Peaks corresponding to SPrYAKYAKL (SEQ ID NO: 7) and CYAKYAKL (SEQ ID NO: 6) were integrated and the extent of ring opening calculated based on the % of the CYAKYAKL (SEQ ID NO: 6) peak. As evident from FIG. 10, a combination of high O-methylhydroxylamine concentration and pH of about 3.5 ensure the complete conversion of the N-terminal thioprolinyl to cysteinyl.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

We claim:

1. A method of synthesizing a polypeptide by ligation of three or more oligopeptide intermediates, the method comprising the steps of:

a) forming a ligation product between an oligopeptide possessing both an N-terminal thiazolidine protected cysteine and a C-terminal thioester, said oligopeptide having the formula:

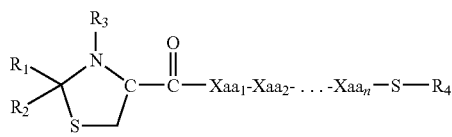

wherein:

n is an integer from 2 to 100;

$R^1$ is selected from H, $C_{1-12}$ alkyl groups optionally substituted with 1-3 substituents selected from halo, nitro, amino, and amino oxycarbonylamino ($H_2N-O-CH_2-CO-NH-$);

$R^2$ is selected from H, $C_{1-12}$ alkyl groups optionally substituted with 1-3 substituents selected from halo, nitro, amino, and amino oxycarbonylamino ($H_2N-O-CH_2-CO-NH-$);

$R^3$ is H or an amino protecting group; and $R^4$ is alkyl having from 1 to 6 carbon atoms or alkylaryl having from 6 to 8 carbon atoms, $-CH_2-CONH_2$, $-CH_2CH_2CONH_2$, or $-(CH_2)_k-CO-X_{aa}$, wherein k is an integer equal to 1 or 2 and Xaa is an amino acid, and a second oligopeptide possessing an N-terminal cysteine;

b) treating the ligation product with a nucleophilic agent under acidic conditions to form a second ligation product having a free N-terminal cysteine; and c) repeating steps a) and b) until the polypeptide is formed.

2. The method of claim 1 further including the step of purifying said prior ligation product prior to said step of forming.

3. The method of claim 2 wherein $R^1$ is selected from the group consisting of H, $-CH_2-NO_2$, $-CH_2Cl$, $-CH_2Br$, $-CHCl_2$, $-CHBr_2$.

4. The method of claim 3 wherein $R^2$ is selected from the group consisting of H, $H_2N-O-CH_2-CO-NH-CH_2-$, $H_2N-O-CH_2-CO-NH-CHCl-$, and $H_2N-O-CH_2-CO-NH-CHBr-$.

5. The method of claim 3 or 4 wherein said nucleophilic agent is an O-alkylhydroxylamine of the formula $H_2N-O-R$, where R is methyl, ethyl, isopropyl, isobutyl, or $-CH_2-COOH$.

6. The method of claim 5 wherein said acidic conditions are in the range of pH 2.0 to pH 6.0.

7. The method of claim 6 wherein $R^1$ and $R^2$ are both hydrogen and wherein $R^3$ is Fmoc, Boc, or Nsc, whenever $R^3$ is said amino protecting group.

8. The method of claim 7 wherein said O-alkylhydroxylamine is O-methylhydroxylamine.

* * * * *